United States Patent [19]

Zollinger

[11] Patent Number: 4,995,867
[45] Date of Patent: Feb. 26, 1991

[54] AURAL MEDICATION DISPENSER

[76] Inventor: Eugene A. Zollinger, 3075 S. State Highway 91, Wellsville, Utah 84339

[21] Appl. No.: 470,193

[22] Filed: Jan. 24, 1990

[51] Int. Cl.⁵ .......................................... A61M 35/00
[52] U.S. Cl. ..................... 604/54; 604/218; 604/289; 222/388
[58] Field of Search ............ 604/57, 59, 64, 77, 604/187, 207, 218, 232, 236, 289, 54; 222/388; 128/864–868

[56] References Cited

U.S. PATENT DOCUMENTS

| | | | |
|---|---|---|---|
| 401,787 | 4/1889 | Lee | 604/64 |
| 1,694,246 | 12/1928 | Boyne | 604/218 |
| 2,541,621 | 2/1951 | Thompson | 604/187 |
| 2,621,655 | 12/1952 | Olson | 604/218 |
| 2,647,512 | 8/1953 | Johnson | 604/64 |
| 2,781,953 | 2/1957 | Sylvander | 222/388 |
| 3,401,692 | 9/1968 | Harris, Jr. | 604/207 |
| 4,135,510 | 1/1979 | Assouly | 604/218 |
| 4,871,094 | 10/1989 | Gall et al. | 604/59 |

FOREIGN PATENT DOCUMENTS

| | | | |
|---|---|---|---|
| 274415 | 7/1988 | European Pat. Off. | 604/187 |
| 339885 | 11/1936 | Italy | 604/218 |
| 87/06456 | 11/1987 | PCT Int'l Appl. | 604/187 |

Primary Examiner—Stephen C. Pellegrino
Assistant Examiner—Ralph A. Lewis
Attorney, Agent, or Firm—Lynn G. Foster

[57] ABSTRACT

A novel aural medication administration device is disclosed which allows a patient to self-administer aural medication to an ear disposed in any plane. Further the aural medication administration device accepts, for later dispensing, drop by drop introduction of medication into a side port of an aural syringe dispenser, the accuracy and precision of each dose of medication being determined by counting drops as prescribed by a physician. By providing for introduction of medication through a side port, rather than through the effluent port, the aural medication administration device can repeatably accept and dispense medication without contaminating a source fluid by material which can collect on the effluent port of an aural dispensing device.

6 Claims, 2 Drawing Sheets

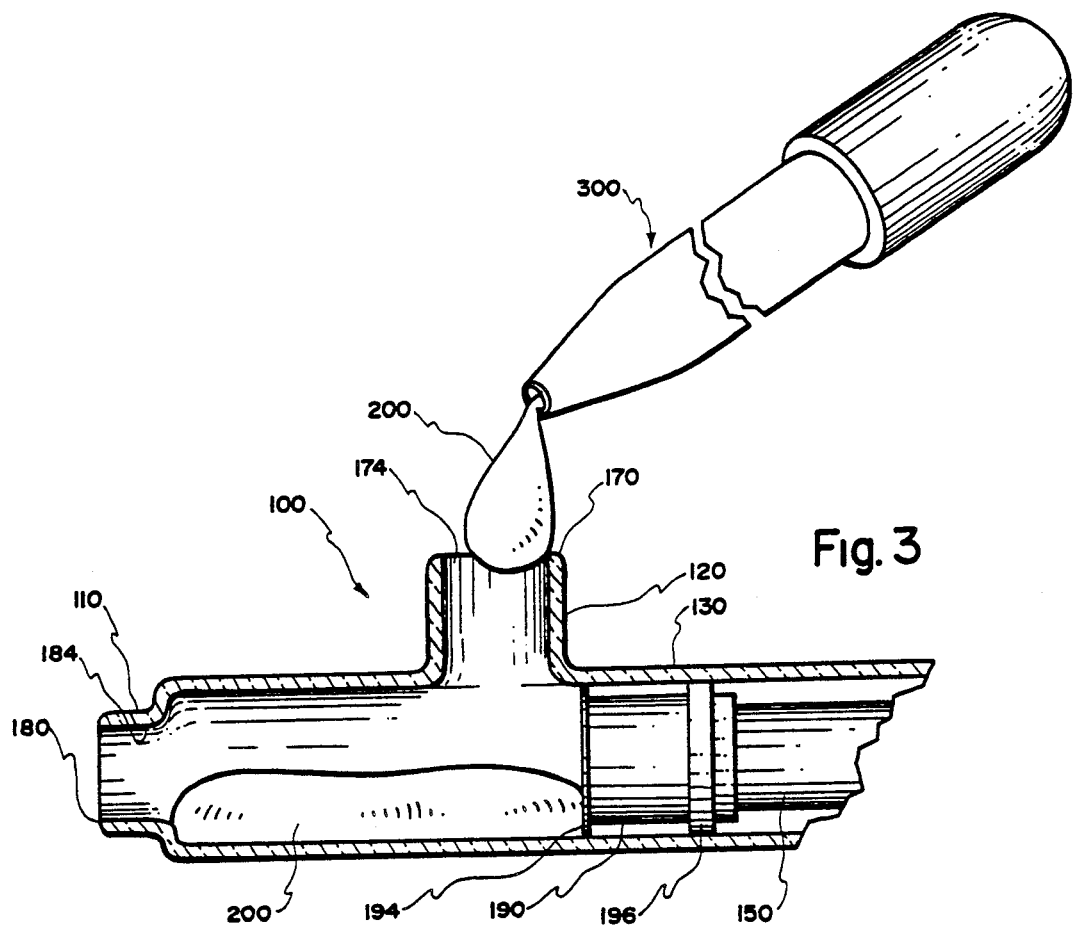
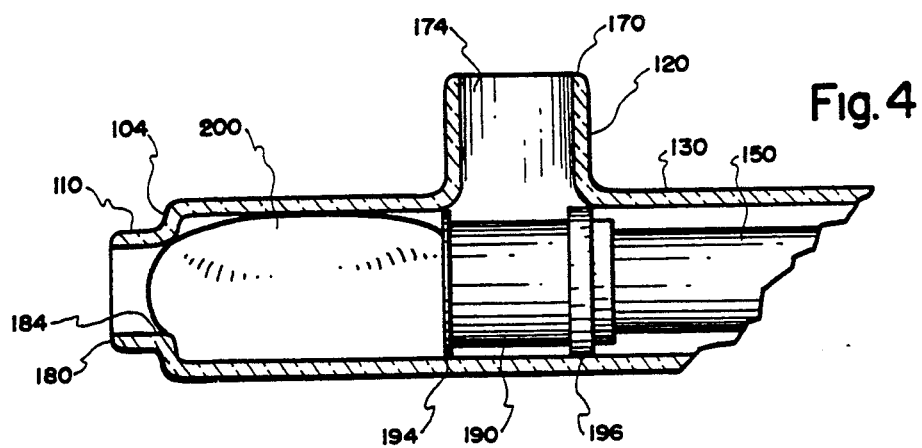

AURAL MEDICATION DISPENSER

FIELD OF INVENTION

This invention applies to medication dispensers and in particular to aural medication dispensers which can provide for determination of dosage measurement by counting drops and for self-medication into the external auditory canal with the ear in any spatial orientation.

PRIOR ART

Aural medications are commonly administered in very small dose volumes. It is a common practice to prescribe the determination of a unit dose by carefully counting drops as they exit an eye dropper or leave a spoon and fall toward a medical patient's horizontally disposed ear. This is a procedure that makes self medication nearly impossible.

The quantity of medication, as normally prescribed, precludes the use of a medical syringe or like instrument because of the difficulty of measurement of a few drops by graduated syringes and, further, use of a syringe will likely contaminate the syringe's effluent portal, thus making repeated use improper without repeated sterilization because reuse would entail dipping the effluent port of the syringe into the source fluid, thereby contaminating it.

BRIEF SUMMARY AND OBJECTS OF THE INVENTION

In brief summary, this novel invention alleviates all of the known problems related to measurement of prescribed doses which require counting drops of medication and to self-administration of aural medication. The invention comprises a device similar to a medical syringe, but comprising a novel barrel with a side port through which medication can be introduced. Medication can be introduced in small volumes, comprising determination by counting the number of drops which fall through the orifice of the side port and therethrough into the barrel of the invention. A plunger inside the barrel can be moved to seal the entry way of the side port to provide an aural medication dispenser which is usable in any spatial orientation. Medication is introduced into an external auditory canal by holding the effluent port of the invention in close proximity to the entry orifice of the ear and rapidly and fully depressing the plunger.

Accordingly, it is a primary object to provide an aural medical fluid dispenser which can receive and dispense medication repeatably without contaminating a source fluid by non-sterile material on the effluent port of the dispenser.

It is a principal object to provide an aural medical fluid dispenser into which fluid can be carefully introduced, providing for drop-by-drop accurate and precise volumetric measurement, as normally prescribed by an attending physician, of small volumes of medication to be introduced into an auditory canal.

It is a dominant object to provide an aural medical fluid dispenser which can be used in any spatial orientation such that a patient can self-administer medication to an ear disposed in any plane.

These and other objects and features of the present invention will be apparent from the detailed description taken with reference to accompanying drawings.

BRIEF DESCRIPTION OF THE DRAWINGS

FIG. 3 is a perspective drawing of a segment of the invention, showing drops of fluid being introduced into a side port, with a segment of barrel cut away to show accumulating fluid and position of a seal at the end of the plunger;

FIG. 4 is a perspective drawing of a segment of the invention, preloaded with fluid, with a segment of the barrel cut away to disclose the seal at the end of the plunger moved distally to seal the side port.

DETAILED DESCRIPTION OF THE ILLUSTRATED EMBODIMENTS

Figure 1:
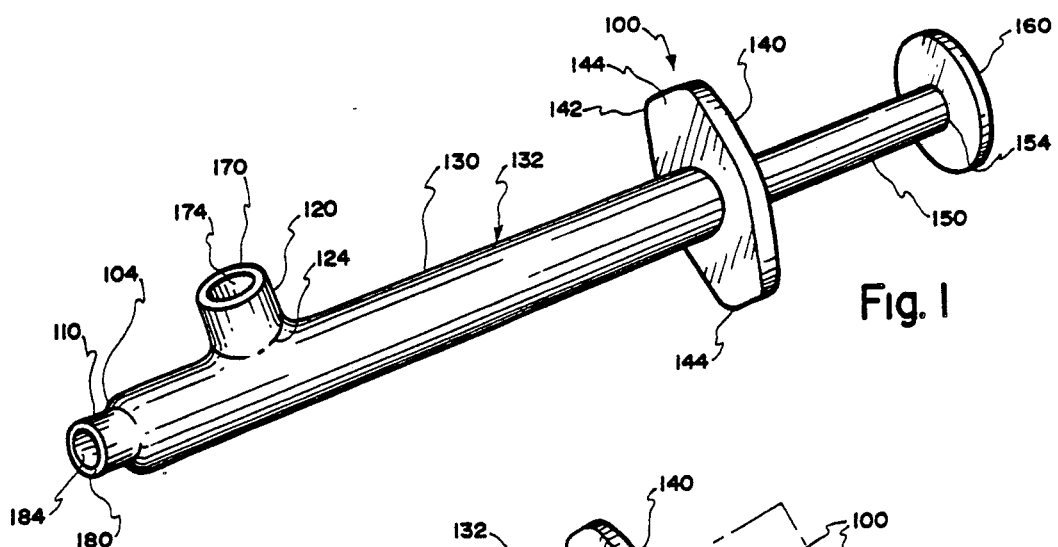
FIG. 1 is a perspective drawing of the invention.
Figure 2:
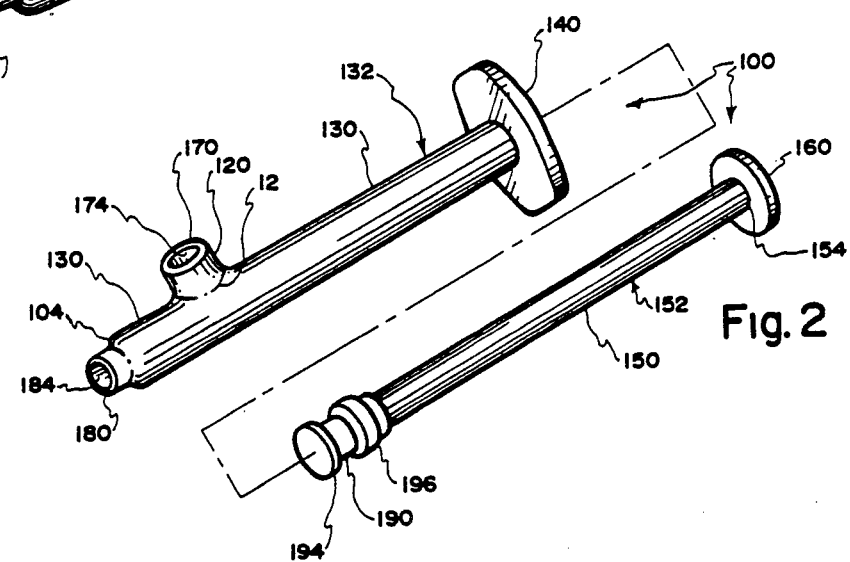
FIG. 2 is a perspective drawing of the invention with the plunger removed and shown beside the barrel.

In this description, the term proximal is used to indicate the segment of the device normally closest to the hand of an operator when it is being used. The term distal refers to the other end. Reference is now made to the embodiments illustrated in FIGS. 1-5 wherein like numerals are used to designate like parts throughout. As seen in FIGS. 1-2, the aural medication device 100 comprises syringe barrel 132 and plunger 152.

Syringe barrel 132 is generally formed of rigid synthetic resinous material although other materials such as stainless steel and glass can be used and comprises hollow barrel 130, proximal barrel end 140, distal end 180, and "T" connection 120. Hollow barrel 130 comprises a long cylindrical shaft of uniform diameter from proximal barrel end 140 to conical part 104 where it necks down to small cylindrical end part 110 at distal end 180.

Hollow barrel 130 is interrupted between the proximal and distal ends by "T" connection 120. "T" connection 120 is formed at interconnection 124 proximal to distal end 180 and far enough removed from distal end 180 that at least an aural medication 200 unit dose can be volumetrically contained in the space between distal end 180 and a plane which lies distal to the most distal connecting point between hollow barrel 130 and "T" connection 120. In this model of the preferred embodiment, the stem of "T" connection 120 comprises round medication entry port 170 and cylindrical medication delivery path 174. Although medication delivery path 174 is cylindrical, entry port 170 is round and "T" connection 120 is normal to hollow barrel 130, other forms for medication port attachment and delivery can be used comprising delivery paths which are funnel shaped, entry ports which are elliptical, and other than normal connections which comprise "Y" connections.

Proximal barrel end 140 ends at plate 142 which is rectangular in shape and orthogonally forms at least two lugs 144 for finger handles to be used to deliver a medication dose as is explained in detail later. A hole (not shown) in the center of plate 142 is juxtaposed with the hollow internal surface of syringe barrel 132 to form the entry port for plunger 152.

Plunger 152 is comprised of two separate parts, plunger shaft 150 and seal 190. In the currently preferred embodiment, plunger shaft is made from rigid synthetic resinous material, although other materials, comprising steel or glass, could be used. On the proximal end 154, button 160 is formed to provide a flat end surface such that lugs 144 and button 160 can be used as opposing surfaces for compressively forcing plunger 152 into syringe barrel 132. Lugs 144 and button 160 can also be used as handles which can be grasped and separated to pull plunger 152 and syringe barrel 132 apart. On the distal end of plunger shaft 150 a retaining knob (not shown) is formed to hold seal 190 firmly attached to plunger shaft 150.

Seal 190 is made from resilient, compressible synthetic resinous material although other materials can be used comprising natural rubber and silicon rubber. Seal 190 is comprised of distal end seal 194 and proximal seal 196 which are separated by cylindrical body 198. Distal end seal 194 and proximal seal 196 are primarily disk-shaped, comprising diameters somewhat larger than the internal diameter of hollow barrel 130 such that, when the disks are inserted into hollow barrel 130, each disk uniformly and slidably compresses against the inner surface of hollow barrel 130 to form a movable seal. The length of cylindrical body 198 is adequate to allow a seal to be maintained in all positions along the length of hollow cylinder 130 where distal end seal 194 and proximal seal 196 have at least partial contact with the inner surface of hollow cylinder 130. Seal 190 comprises a fitting (not shown) which compressibly connects to the knob on the distal end of plunger shaft 150.

As indicated earlier, distal end 180 of hollow cylinder 132 is formed where hollow barrel 130 necks downward at conical section 104. The internal surface shape and the position of conical shape 104 forms a nozzle 184 for fluid flowing from distal end 180. In addition, inward travel of conical shape 104 forms a distal stop for plunger 152. The opposing faces of the internal surface of conical shape 104 and end seal 194 are shaped to match such that there is minimum dead space between the internal face of conical shape 104 and the end seal 194 when plunger 152 is fully depressed against the distal stop formed by conical shape 104. For the same reason, the length of distal end 180 is held to a minimum, also providing minimum dead space so that the volumes of small unit doses are not detrimentally reduced.

To use the invention, pull plunger 152 proximally from distal end 180 of syringe barrel 132 until plunger shaft 150 and seal 190 are clear of cylindrical medication delivery path 174. Orient aural medication device 100 such that cylindrical medication delivery path 174 opens vertically upward. Position a device which produces accurate and precise drop volumes, such as eye dropper 300 shown in FIG. 3, directly above cylindrical medication delivery path 174. Carefully deposit the prescribed number of drops into cylindrical medication delivery path 174. When the unit dose has been introduced into the delivery path and therefrom into syringe barrel 132, remove eye dropper 300 and close cylindrical medication delivery path 174, as shown in FIG. 4.

To close delivery path 174, move plunger 152 distally until distal end seal 194 seals the distal portion of hollow cylinder 130 from cylindrical medication delivery path 174. The unit dose of medication 200 is so held in the chamber formed by hollow cylinder 130 and distal end seal 194 that aural medication 200 can delivered in any orientation of aural medication device 100 providing opportunity for medicating and, in particular, for self-medicating an ear in planar orientation other than horizontal.

Figure 5:
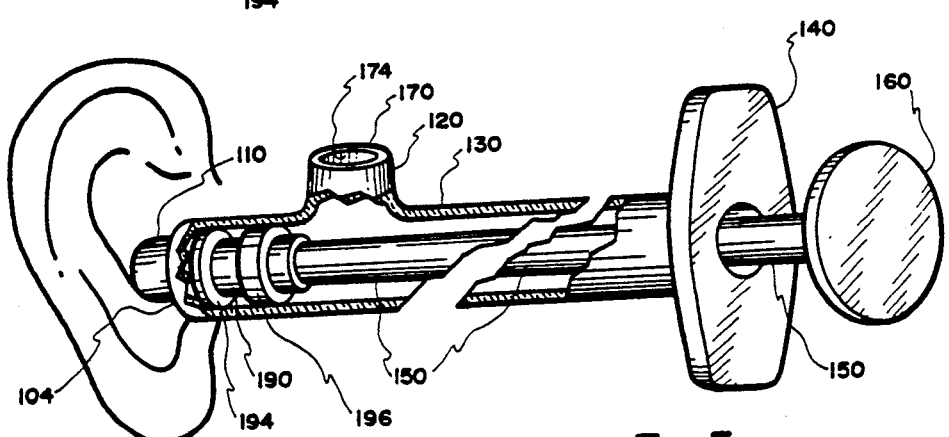
FIG. 5 is a perspective view of the invention shown in close proximity to an entry orifice of an external auditory canal of an ear and further showing, via a cut away segment, the further most distal position of the plunger seal.

FIG. 5 shows position of aural medication device 100 positioned normal to the plane of the ear and plunger 152 completely depressed into the syringe barrel 132 as is the case at the end of delivery of an aural medication 200.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method for repeatably delivering medication using a single aural medication dispensing device without contaminating source medical fluid comprising the following steps:

(a) provide an aural medical dispensing device comprising:

plunger means for moving and sealing fluid within a syringe barrel means, the plunger means comprising:

rod means of sufficient length to drive substantially all fluid residing within the syringe barrel means through a distal port means of the syringe barrel means;

seal means on the distal end of the plunger means comprising:

seal end means on the distal end of the seal means which can seal and wipe the inner surface of the syringe barrel means as it is moved distally to drive fluid toward the distal port means of the syringe barrel means;

seal length means, contiguous with and extending proximal from the seal end means, which provide lateral stability to the seal means and rod means to provide seal integrity as the seal means is moved past an open side port means of the syringe barrel means;

syringe barrel means comprising:

proximal entry port means for the plunger means;

distal effluent port means from which fluid can be dispensed into an external auditory canal; and side port means into which medical fluid can be introduced without the inserted fluid being contaminated by material on the distal effluent port means and which is positioned sufficiently proximal from the distal effluent port means that a unit dose can be stored and sealed by the plunger seal means without leakage from the distal effluent port means;

(b) pull the plunger means proximally from the distal end of the syringe barrel means until the seal means is clear of the entry space of the side port means of the syringe barrel means;

(c) holding the syringe barrel such that the side port means opens vertically upward and using an eye dropper or the like transfer medication through the side port means into the syringe barrel means;

(d) after a unit dose is contained in the syringe barrel means, move the plunger means distally until the seal means seals the medication from the entry side port means;
(e) place the distal effluent port means at the entry orifice of the external auditory canal and push the plunger means to the distal end of the syringe barrel means discharging the medication dose into the ear;
(f) return to step (b) to repeat as necessary.

2. A method for repeat medication using a single aural medication dispensing device according to claim 1 whereby step (c) further comprises counting drops as prescribed for dosage determination to provide a unit dose of medication within the syringe barrel means.

3. A method for providing aural medication as prescribed, by counted drops, using an aural medication dispensing device comprising the following steps:
(a) provide an aural medical dispensing device comprising:
    plunger means for moving and sealing fluid within a syringe barrel means, the plunger means comprising:
        rod means of sufficient length to drive substantially all fluid residing within the syringe barrel means through a distal port means of the syringe barrel means;
        seal means on the distal end of the plunger means comprising:
            seal end means on the distal end of the seal means which can seal and wipe the inner surface of the syringe barrel means as it is moved distally to drive fluid toward the distal port means of the syringe barrel means;
            seal length means, contiguous with and extending proximal from the seal end means, which provide lateral stability to the seal means and rod means to provide seal integrity as the seal means is moved past an open side port means of the syringe barrel means;
    syringe barrel means comprising:
        proximal entry port means for the plunger means;
        distal effluent port means from which fluid can be dispensed into an external auditory canal; and
        side port means into which medical fluid can be introduced as prescribed by counting drops and which is positioned sufficiently proximal from the distal effluent port means that a unit dose can be stored and sealed by the plunger seal means without leakage from the distal effluent port means;
(b) pull the plunger means proximally from the distal end of the syringe barrel means until the seal means is clear of the entry space of the side port means of the syringe barrel means;
(c) holding the syringe barrel such that the side port means opens vertically upward and using an eye dropper or the like, drop by drop transfer medication into the syringe barrel means through the side port means, continuing until the prescribed dosage is transferred into the syringe barrel means;
(d) after the prescribed unit dose is deposited in the syringe barrel means, move the plunger means distally until the seal means seals the medication from the entry side port means;
(e) place the distal effluent port means at the entry orifice of the external auditory canal and push the plunger means to the distal end of the syringe barrel means discharging the medication dose into the ear;

4. A method for providing aural medication as prescribed, by counted drops, using a single aural medication dispensing device according to claim 3 whereby repeat self-medication using a single aural medication dispensing device without contaminating source medical fluid comprises repeating the steps (b) through (e), as necessary.

5. A method of self-administering of liquid medication to one's ear comprising the steps of:
    retracting a plunger within a barrel of a syringe having a hollow interior and a distal port aligned with the plunger until the hollow of the barrel is exposed at a side medication influent port;
    introducing a selected amount of ear medication in liquid form through the side port into the hollow of the barrel;
    advancing the plunger until the barrel is not open at the side port while substantially retaining the liquid ear medication within the barrel;
    user placing the distal port into the ear of the user and user advancing the plunger within the barrel to discharge the liquid ear medication from the barrel into the ear.

6. A method of administering of liquid medication to one's ear comprising the steps of:
    retracting a plunger within a barrel of a syringe having a hollow interior and a distal port aligned with the plunger until the hollow of the barrel is exposed at a side medication influent port;
    introducing a selected amount of ear medication in liquid form through the side port into the hollow of the barrel;
    advancing the plunger until the barrel is first not open at the side port and thereafter discharge the liquid ear medication from the barrel into the ear.

* * * * *